US008999985B2

(12) United States Patent
Gao (10) Patent No.: US 8,999,985 B2
(45) Date of Patent: Apr. 7, 2015

(54) SUBSTITUTED PHTHALAZIN-1(2H)-ONES, PREPARATION PROCESSES AND MEDICAL USES THEREOF

(75) Inventor: Daxin Gao, Shanghai (CN)

(73) Assignee: Shanghai de Novo Pharmatech Co Ltd., Shanghai (CN)

( * ) Notice: Subject to any disclaimer, the term of this patent is extended or adjusted under 35 U.S.C. 154(b) by 0 days.

(21) Appl. No.: 13/882,346

(22) PCT Filed: Dec. 2, 2010

(86) PCT No.: PCT/CN2010/001942
§ 371 (c)(1),
(2), (4) Date: Apr. 29, 2013

(87) PCT Pub. No.: WO2012/071684
PCT Pub. Date: Jun. 7, 2012

(65) Prior Publication Data
US 2013/0224107 A1     Aug. 29, 2013

(51) Int. Cl.
| | |
|---|---|
| *A61K 31/502* | (2006.01) |
| *C07D 237/32* | (2006.01) |
| *C07D 403/12* | (2006.01) |
| *C07D 405/12* | (2006.01) |
| *C07D 405/14* | (2006.01) |
| *C07D 487/08* | (2006.01) |
| *A61K 31/4188* | (2006.01) |
| *A61K 31/551* | (2006.01) |
| *A61K 45/06* | (2006.01) |

(52) U.S. Cl.
CPC ............ *A61K 31/502* (2013.01); *C07D 237/32* (2013.01); *C07D 403/12* (2013.01); *C07D 405/12* (2013.01); *C07D 405/14* (2013.01); *C07D 487/08* (2013.01); *A61K 31/4188* (2013.01); *A61K 31/551* (2013.01); *A61K 45/06* (2013.01)

(58) Field of Classification Search
CPC ............................ A61K 31/502; C07D 237/32
USPC .......................................... 514/248; 544/237
See application file for complete search history.

(56) References Cited

U.S. PATENT DOCUMENTS

| | | | |
|---|---|---|---|
| 5,177,075 | A | 1/1993 | Suto et al. |
| 2002/0028815 | A1 | 3/2002 | Ator et al. |
| 2003/0134843 | A1 | 7/2003 | Lubisch et al. |
| 2004/0067949 | A1 | 4/2004 | Grandel et al. |

FOREIGN PATENT DOCUMENTS

| | | | |
|---|---|---|---|
| WO | 9833802 | A1 | 8/1998 |
| WO | 9911622 | A1 | 3/1999 |
| WO | 9911623 | A1 | 3/1999 |
| WO | 9911628 | A1 | 3/1999 |
| WO | 9911644 | A1 | 3/1999 |
| WO | 9911649 | A1 | 3/1999 |
| WO | 9911945 | A1 | 3/1999 |
| WO | 9959973 | A1 | 11/1999 |
| WO | 9959975 | A1 | 11/1999 |
| WO | 0039070 | A1 | 7/2000 |
| WO | 0039104 | A1 | 7/2000 |
| WO | 2004080976 | A1 | 9/2004 |
| WO | 2005012305 | A2 | 2/2005 |
| WO | 2009004356 | A1 | 1/2009 |
| WO | WO 2012/071684 | * | 6/2012 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report dated Sep. 1, 2011 for PCT/CN2010/001942.
Nuala McCabe, et al., Deficiency in the Repair of DNA Damage by Homologous Recombination and Sensitivity to Poly(ADP-Ribose) Polymerase Inhibition, Cancer Research, Aug. 15, 2006, 66: (16), pp. 8109-8115.
Helen E. Bryant, et al, Specific killing of BRCA2-deficient tumours with inhibitors of poly(ADP-ribose) polymerase, Letters to Nature, Apr. 14, 2005, pp. 913-920, vol. 434, UK.
Hannah Farmer, et al., Targeting the DNA repair defect in BRCA mutant cells as a therapeutic strategy, Letters to Nature, Apr. 14, 2005, pp. 917-921, vol. 434, UK.

* cited by examiner

*Primary Examiner* — Douglas M Willis
(74) *Attorney, Agent, or Firm* — Lowe Hauptman & Ham, LLP (57) ABSTRACT

Disclosed are substituted phthalazin-1 (2H)-ones of the formula (IA), preparation processes and medical uses thereof, particularly related to the compositions containing the same and the uses thereof, more particularly related to their pharmaceutical use as inhibitors of PARP.

7 Claims, 1 Drawing Sheet

SUBSTITUTED PHTHALAZIN-1(2H)-ONES, PREPARATION PROCESSES AND MEDICAL USES THEREOF

The present application is national phase of International Application No. PCT/CN2010/001942, filed Dec. 2, 2010, the disclosures of which are hereby incorporated by reference herein in their entirety.

FIELD

The present invention relates to new heterocyclic derivatives, methods for making them, compositions containing the same and the uses thereof, particularly to their pharmaceutical use as inhibitors of PARP.

BACKGROUND

PARP is short for "poly (ADP-ribose) polymerase". Cancer cells use the enzyme PARP to repair DNA damage, including the damage inflicted by chemotherapy drugs. Researchers are examining whether drugs that inhibit the enzyme PARP will diminish this self-repair mechanism and make cancer cells more sensitive to the treatment and promotion of cancer cell death.

PARP inhibitors are a group of pharmacological inhibitors of the enzyme Poly ADP ribose polymerase (PARP), which is important for facilitating DNA repair, controlling RNA transcription, mediating cell death and regulating immune response. Therefore, the PARP inhibitors are developed for multiple indications; the most important indication is cancer. Several types of cancer are more dependent on PARP than regular cells, making PARP an attractive target for chemotherapeutic cancer therapy.

There is considerable interest in the development of PARP inhibitors as chemo sensitizers for use in cancer therapy and to limit cellular damage after ischemia or endotoxic stress. Cytotoxic drugs, generally, or radiation can induce activation of PARP, and it has been demonstrated that inhibitors of PARP can potentiate the DNA damaging and cytotoxic effects of chemotherapy and irradiation (see Kock, et al, 45, J. Med. Chem. 4961, 2002). PARP mediated DNA repair in response to DNA damaging agents represents a mechanism for drug resistance in tumors, and the inhibition of this enzyme has been shown to enhance the activity of ionizing radiation and several cytotoxic antitumor agents, including temozolomide and topotecan. Suto et al, in U.S. Pat. No. 5,177,075, disclosed several isoquino lines used for enhancing the lethal effects of ionizing radiation or chemotherapeutic agents on tumor cells. Weltin et al, "Effect of 6(5H)-Phenanthridinone, an Inhibitor of Poly (ADP-ribose) Polymerase, on Cultured Tumor Cells", Oncol. Res., 6:9, 399-403 (1994) disclosed that the inhibition of PARP activity reduced proliferation of tumor cells, and produced a marked synergistic effect when tumor cells are co-treated with an alkylating drug. PARP is thus a potentially important therapeutic target for enhancing DNA-damaging cancer therapies.

PARP inhibitors can also inhibit the growth of cells having defects in the homologous recombination (HR) pathway of double-stranded DNA repair, see, for example, Bryant et al, "Specific killing of BRCA2-deficient tumors with inhibitors of poly (ADP-ribose) polymerase," Nature 434, 913 (2005); Farmer et al, "Targeting the DNA repair defect in BRCA mutant cells as a therapeutic strategy," Nature 434, 917 (2005). This effect operates without the presence of chemosensitizers. Known states associated with HR defects include BRCA-1 defects, BRCA-2 defects, and Fanconi anemia-associated cancers (McCabe et al., "Deficiency in the Repair of DNA Damage by Homologous Recombination and Sensitivity to Poly (ADP-Ribose) Polymerase Inhibition," Cancer Res. 66. 8109, 2006). Proteins identified as associated with Fanconi anemia include FANCA, FANCB, FANCC, FANCD2, FANCE, FANCF, FANCG, FANCL, and FANCM. Id. For reviews, see Zaremba et al., "PARP Inhibitor Development for Systemic Cancer Targeting," Anti-Cancer Agents in Medicinal Chemistry 7, 515 (2007), and Lewis et al., "Clinical poly(ADP-ribose) polymerase inhibitors for the treatment of cancer," Curr. Opin. Investigational Drugs 8, 1061 (2007).

Large numbers of known PARP inhibitors have been described in Banasik et al., "Specific Inhibitors of Poly (ADP-Ribose) Synthetase and Mono (ADP-Ribose)-Transferase", J. Biol. Chem., 267:3, 1569-75 (1992), and in Banasik et al., "Inhibitors and Activators of ADP-Ribosylation Reactions", Molec. Cell. Biochem., 138, 185-97 (1994).

In addition to the above, PARP inhibitors have been disclosed and described in the following international patent applications: WO09/04356, WO04/80976, WO 00/42040; WO00/39070; WO00/39104; WO99/11623; WO99/11628; WO99/11622; WO 99/59975; WO99/11644; WO99/11945; WO99/11649; and WO99/59973. PARP-inhibitors that potentiate the lethality of cytotoxic agents by chemosensitizing tumor cells to the cytotoxic effects of chemotherapeutic agents has been reported in, inter alia, US2002/0028815; US2003/0134843; US2004/0067949; White A W, et al., 14 Bioorg. and Med. Chem. Letts. 2433 (2004); Canon Koch S S, et al., 45 J. Med. Chem. 4961 (2002); Skalitsky D J, et al, 46 J. Med. Chem. 210 (2003); Farmer H, et al, 434 Nature 917 (14 Apr. 2005); Plummer E R, et al., 11(9) Clin. Cancer Res. 3 402 (2005); Tikhe J G, et al., 47 J. Med. Chem. 5467 (2004); Griffin R. J., et al, WO98/33802; and Helleday T, et al, WO2005/012305.

In addition to cancer therapy, PARP inhibitors are considered as a potential drug for acute, life-threatening diseases, such as stroke and myocardial infarction, diabetes, inflammation, as well as a long-term drug for neurodegenerative diseases (Graziani G, Szabó C (July 2005). "Clinical perspectives of PARP inhibitors". Pharmacol. Res. 52 (1): 109-18).

SUMMARY

The present inventors have now discovered a series of new heterocyclic compounds. These compounds are characterized by having a heterocyclic ring represented by Q, wherein Q is attached by —CO—CO—R group at one of the two nitrogen atoms of the heterocyclic ring, as well as attached by —CO—B-A group at another nitrogen atom. The compounds exhibit a surprising increase in the level of inhibition of the activity of PARP enzyme, and/or in the level of potentiation of tumor cells to radiotherapy and various chemotherapies, and/or a surprising increase in the solubility of the compound (in aqueous media and/or phosphate buffer solution)-enhanced solubility may be of use in formulation of the compounds, for example, for administration via IV route, or for oral formulations (e.g. liquid and small tablet forms) for adult and pediatric use. The oral bioavailability of the compounds of the present invention may be enhanced. The compounds may also be less susceptible to the action of MDR1 in cells.

Accordingly, the first aspect of the present invention provides a compound of the formula (I), and hydrates, isomers, solvates, prodrugs, pharmaceutical composition containing them, and pharmaceutically acceptable salts thereof:

B-A-CO-Q-CO—CO—R   (I)

Wherein:

A is aryl or substituted aryl; or heteroaryl or substituted heteroaryl, said substituents for A are selected from halo, cyano, lower alkyl, amino, lower alkylamino, sulfonamide, hydroxyl, lower alkyl alkyoxyl, and alkyl substituted by optionally substituted heterocyclic group or optionally substituted aryl;

B is aryl or substituted aryl; or heteroaryl or substituted heteroaryl, said substituents for B are selected from halo, cyano, lower alkyl, amino, lower alkylamino, sulfonamide, hydroxyl, lower alkyl alkyoxyl, and alkyl substituted by optionally substituted heterocyclic group or optionally substituted aryl;

Q is optionally substituted heterocyclic ring which contains at least two nitrogen atoms as a member of the atoms forming the ring, wherein the at least two nitrogen atoms independently bind to —CO-A-B group and CO—CO—R group at the carbon atom of carbonyl, respectively; and is selected from the group consisting of mono-heterocyclic group, bi-heterocyclic group, bridged-heterocyclic group, and spiro-heterocyclic group; and R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl, and heteroaryl or substituted heteroaryl, said substituents are selected from the group consisting of halo, lower alkyl, amino, lower alkylamino, lower alkyl alkyoxyl, haloalkoxyl, hydroxyl, amido, aminocarbonyl, sulfonamide, cyano, alkynyl, alkoxyl, aryloxyl, carboxylic acid, and carboxylic ester.

One subset of compounds of the present invention which is of interest relates to compounds of formula (IA), and hydrates, isomers, solvates, prodrugs, pharmaceutical composition containing them, and pharmaceutically acceptable salts thereof:

(IA)

Wherein:

Ar can be aryl and Het can be heteroaryl;

$Z_1$ can be C—$R_1$ or N;

Q is optionally substituted heterocyclic ring which contains at least two nitrogen atoms as a member of the atoms forming the ring wherein the at least two nitrogen atoms independently bind to —CO-A-B group and CO—CO—R group at the carbon atom of carbonyl, respectively; and is selected from the group consisting of mono-heterocyclic group, bridged-heterocyclic group, bi-heterocyclic group and spiro-heterocyclic group;

R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl and heteroaryl or substituted heteroaryl, said substituents are selected from the group consisting of halo, lower alkyl, amino, lower alkylamino, lower alkyl alkyoxyl, haloalkoxyl, hydroxyl, amido, aminocarbonyl, sulfonamide, cyano, alkynyl, alkoxyl, aryloxyl, carboxylic acid, and carboxylic ester; and $R_1$ and $R_2$ are each independently selected from the group consisting of hydrogen, optionally substituted alkyl, optionally substituted cycloalkyl, optionally substituted aryl, optionally substituted heteroaryl, haloalkoxyl, hydroxyl, amino, alkylamino, amido, aminocarbonyl, sulfonamide, cyano, alkynyl, alkoxyl, aryloxyl, carboxylic acid, carboxylic ester, and halogen.

Another subset of compounds of the present invention which is of interest relates to compounds of formula (IB), and hydrates, isomers, solvates, prodrugs, pharmaceutical composition containing them, and pharmaceutically acceptable salts thereof:

(IB)

Wherein:

Ar can be aryl and Het can be heteroaryl;

$Z_1$ can be C—$R_1$ or N;

R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl and heteroaryl or substituted heteroaryl, said substituents are selected from the group consisting of halo, lower alkyl, amino, lower alkylamino, and lower alkyl alkyoxyl, haloalkoxyl, hydroxyl, amido, aminocarbonyl, sulfonamide, cyano, alkynyl, alkoxyl, aryloxyl, carboxylic acid, and carboxylic ester; and $R_1$ and $R_2$ are each independently selected from the group consisting of hydrogen, optionally substituted alkyl, optionally substituted cycloalkyl, optionally substituted aryl, optionally substituted heteroaryl, haloalkoxyl, hydroxyl, amino, alkylamino, amido, aminocarbonyl, sulfonamide, cyano, alkynyl, alkoxyl, aryloxyl, carboxylic acid, carboxylic ester, and halogen; and represents a heterocyclic group selected from but not limited to:

Another subset of compounds of the present invention which is of interest relates to compounds of formula (IC), and hydrates, isomers, solvates, prodrugs, pharmaceutical composition containing them, and pharmaceutically acceptable salts thereof:

(IC)

Wherein:
$Z_1$ can be C—$R_1$ or N;
$Z_2$ can be C or N;
R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl and heteroaryl or substituted heteroaryl, said substituents are selected from the group consisting of halo, lower alkyl, amino, lower alkylamino, and lower alkyl alkyoxyl, haloalkoxyl, hydroxyl, amido, aminocarbonyl, sulfonamide, cyano, alkynyl, alkoxyl, aryloxyl, carboxylic acid, and carboxylic ester; and
$R_1$ and $R_2$ are each independently selected from the group consisting of hydrogen, optionally substituted alkyl, optionally substituted cycloalkyl, optionally substituted aryl, optionally substituted heteroaryl, haloalkoxyl, hydroxyl, amino, alkylamino, amido, aminocarbonyl, sulfonamide, cyano, alkynyl, alkoxyl, aryloxyl, carboxylic acid, carboxylic ester, and halogen.

Another subset of compounds of the present invention which is of interest relates to compounds of formula (ID), and hydrates, isomers, solvates, prodrugs, pharmaceutical composition containing them, and pharmaceutically acceptable salts thereof:

(ID)

Wherein:
$Z_1$ can be C—$R_1$ or N;
$Z_2$ can be C or N;
R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl and heteroaryl or substituted heteroaryl, said substituents are selected from the group consisting of halo, lower alkyl, amino, lower alkylamino, and lower alkyl alkyoxyl, haloalkoxyl, hydroxyl, amido, aminocarbonyl, sulfonamide, cyano, alkynyl, alkoxyl, aryloxyl, carboxylic acid, and carboxylic ester, and
$R_1$ and $R_2$ are each independently selected from the group consisting of hydrogen, optionally substituted alkyl, optionally substituted cycloalkyl, optionally substituted aryl, optionally substituted heteroaryl, haloalkoxyl, hydroxyl, amino, alkylamino, amido, aminocarbonyl, sulfonamide, cyano, alkynyl, alkoxyl, aryloxyl, carboxylic acid, carboxylic ester, and halogen.

Another subset of compounds of the present invention which is of interest relates to compounds of formula (IE): and hydrates, isomers, solvates, prodrugs, pharmaceutical composition containing them, and pharmaceutically acceptable salts thereof:

(IE)

Wherein:
$Z_1$ can be C—$R_1$ or N;
$Z_2$ can be C or N;

R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl and heteroaryl or substituted heteroaryl, said substituents are selected from the group consisting of halo, lower alkyl, amino, lower alkylamino, and lower alkyl alkyoxyl, haloalkoxyl, hydroxyl, amido, aminocarbonyl, sulfonamide, cyano, alkynyl, alkoxyl, aryloxyl, carboxylic acid, and carboxylic ester; and $R_1$ and $R_2$ are each independently selected from the group consisting of hydrogen, optionally substituted alkyl, optionally substituted cycloalkyl, optionally substituted aryl, optionally substituted heteroaryl, haloalkoxyl, hydroxyl, amino, alkylamino, amido, aminocarbonyl, sulfonamide, cyano, alkynyl, alkoxyl, aryloxyl, carboxylic acid, carboxylic ester, and halogen.

The second aspect of the present invention provides a pharmaceutical composition comprising the compounds of formula (I), (IA), (IB), (IC), (ID), or (IE), hydrates, isomers, solvates, pharmaceutical composition containing them or pharmaceutically acceptable salts thereof in an effective therapeutic dose, as well as a pharmaceutically acceptable carrier, adjuvant, or vehicle.

A third aspect of the present invention provides use of the compounds of the present disclosure, hydrates, isomers, solvates, pharmaceutical composition containing them or pharmaceutical acceptable salts thereof in the preparation of a medicament as a PARP inhibitor.

A fourth aspect of the present invention provides use of a compound as defined in the first aspect of the invention in the preparation of a medicament for:

(a) preventing poly (ADP-ribose) chain formation by inhibiting the activity of cellular PARP enzyme.

(b) the treatment of the following diseases: vascular disease; septic shock; ischaemic injury, both cerebral and cardiovascular; reperfusion injury, both cerebral and cardiovascular; neurotoxicity, including acute and chronic treatments for stroke and Parkinson's disease; haemorraghic shock; eye related oxidative damage; transplant rejection; inflammatory diseases, such as arthritis, inflammatory bowel disease, ulcerative colitis and Crohn's disease; multiple sclerosis; secondary effects of diabetes; as well as the acute treatment of cytoxicity following cardiovascular surgery; pancreatitis; atherosclerosis; or diseases ameliorated by the inhibition of the activity of PARP;

(c) use as an adjunct in cancer therapy or for potentiating tumor cells to the treatment with ionizing radiation or chemotherapeutic agents.

In particular, compounds as defined in the first aspect of the invention can be used in anti-cancer combination therapies (or as adjuncts) along with alkylating agents, such as methyl methanesulfonate (MMS), temozolomide and dacarbazine (DTIC); also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles; also dual topoisomerase-I and II inhibitors like the benzophenazines, XR 11576/MLN 576 and benzopyridoindoles; platinum based anticancer drugs Carboplatin, Cisplatin and Oxaliplatin. Such combinations could be given, for example, as intravenous preparations or by oral administration, dependenting on the preferred method of administration for the particular agent.

Other further aspects of the invention provide methods for the treatment of disease ameliorated by the inhibition of PARP, comprising administering to a subject in need of the treatment a therapeutically-effective amount of a compound as defined in the first aspect, preferably in the form of a pharmaceutical composition; and methods for the treatment of cancer, comprising administering to a subject in need of the treatment a therapeutically-effective amount of a compound as defined in the first aspect in combination, preferably in the form of a pharmaceutical composition, simultaneously or sequentially with radiotherapy (ionizing radiation) or chemotherapeutic agents.

In further aspects of the present invention, the compounds may be used in the preparation of a medicament for the treatment of cancer which is deficient in Homologous Recombination (HR) dependent DNA double strand break (DSB) repair pathway, or in the treatment of a patient with a cancer is deficient in HR dependent DNA DSB repair pathway, comprising administering to said patient a therapeutically-effective amount of the compound.

DETAILED DESCRIPTION OF THE DISCLOSURE

Unless otherwise stated, the following terms used in the specification and claims have the meanings defined below.

The term "alkyl" refers to a saturated aliphatic hydrocarbon group including $C_1$-$C_{20}$ straight chain and branched chain groups. Preferably, an alkyl group is a moderate size alkyl having 1 to 10 carbon atoms, e.g., methyl, ethyl, propyl, 2-propyl, n-butyl, iso-butyl, tert-butyl, pentyl, and the like. More preferably, it is a lower alkyl having 1 to 4 carbon atoms, e.g., methyl, ethyl, propyl, 2-propyl, n-butyl, iso-butyl, or tert-butyl, and the like. The term "optionally substituted alkyl" refers to an alkyl group which may be substituted by one to four substituents selected from the group consisting of halo, hydroxyl, lower alkoxy, aryl (optionally substituted with one or more groups which each independently is halo, hydroxy, lower alkyl or lower alkoxy groups), aryloxy (optionally substituted with one or more groups which each independently is halo, hydroxy, lower alkyl or lower alkoxy groups), heteroaryl (optionally substituted with one or more groups which each independently is halo, hydroxy, lower alkyl or lower alkoxy groups), heterocycloalkyl(optionally substituted with one or more groups which each independently is halo, hydroxy, lower alkyl or lower alkoxy groups), haloalkoxyl, amino, alkylamino, amido, aminocarbonyl, cyano, alkynyl, alkoxyl, aryloxyl, carboxylic acid, and carboxylic ester.

The term "cycloalkyl" refers to a 3 to 8 membered all-carbon monocyclic ring, an all-carbon 3-membered/6-membered, 4-membered/6-membered, 5-membered/6-membered or 6-membered/-membered fused bicyclic ring or a multicyclic fused ring (a "fused" ring system means that each ring in the system shares an adjacent pair of carbon atoms with other ring in the system) group wherein one or more rings may contain one or more double bonds, but none of the rings has a completely conjugated pi-electron system. Examples of cycloalkyl groups are cyclopropyl, cyclobutyl, cyclopentyl, cyclopentenyl, chcyclohexyl, cyclohexadienyl, adamantyl, cycloheptyl, cycloheptatrienyl, and the like. The cycloalkyl group may be substituted or unsubstituted. When substituted, the substituent group(s) is preferably one or more independently selected from the group consisting of lower alkyl, trihaloalkyl, halo, hydroxy, amino, lower alkylamino, lower alkylalkoxy, cyano, acyl, thioacyl, carboxylic acid, carboxylic ester, mercapto, lower alkoxy, aryl (optionally substituted with one or more groups which each independently is halo, hydroxy, lower alkyl or lower alkoxy groups), aryloxy (optionally substituted with one or more groups which each independently is halo, hydroxy, lower alkyl or lower alkoxy groups), 6-membered heteroaryl (having 1 to 3 nitrogen atoms on the ring, the carbons on the ring being optionally substituted with one or more groups which each independently is halo, hydroxy, lower alkyl or lower alkoxy groups), 5-membered heteroaryl (having 1 to 3 heteroatoms selected from the group consisting of nitrogen, oxygen and sulfur, the carbon and nitrogen atoms of the group being optionally substituted with one or more groups which each independently is halo, hydroxy, lower alkyl or lower alkoxy groups), 5- or 6-membered heterocyclic alkyl [having 1 to 3 heteroatoms selected from the group consisting of nitrogen, oxygen and sulfur, the carbon and nitrogen (if present) atoms of the group being optionally substituted with one or more groups which each independently is halo, hydroxy, lower alkyl or lower alkoxy groups, mercapto, lower alkyl, arylthio (optionally substituted with one or more groups which each independently is halo, hydroxy, lower alkyl or lower alkoxy groups)], cyano, acyl, thioacyl, O-carbamyl, N-carbamyl, O-thio carbamyl, N-thiocarbamyl, C-amido, N-amido, nitro, N-sulfonamido, and S-sulfonamido.

The term "alkenyl" refers to an alkyl group as defined above having at least 2 carbon atoms and at least one carbon-carbon double bond. Representative examples include, but are not limited to ethenyl, 1-propenyl, 2-propenyl, 1-butenyl, 2-butenyl, 3-butenyl, and the like. The term "optionally substituted alkenyl" means the alkenyl which may be substituted with one or more groups which each independently is halo, cyano, lower alkyl or lower alkoxy groups.

The term "alkynyl" refers to an alkyl group as defined above having at least 2 carbon atoms and at least one carbon-carbon triple bond. Representative examples include, but are not limited to ethynyl, 1-propynyl, 2-propynyl, 1-butynyl, 2-butynyl, 3-butynyl, and the like. The term "optionally substituted alkenyl" means the alkynyl which may be substituted with one or more groups which each independently is halo, cyano, lower alkyl or lower alkoxy groups.

The term "aryl" refers to groups having at least one aromatic ring, i.e., having a conjugated pi-electron system, including all-carbon cyclic aryl, heteroaryl and biaryl group. Examples of aryl include phenyl, nathathyl. Said aryl group may be optionally substituted with one or more groups which are each independently selected from the group consisting of halo, trihalomethyl, hydroxy, amino, lower alkylamino, sulfonamide, mercapto, alkylthio, nitro, cyano, alkoxyl, and alkyl.

The term "heteroaryl" refers to an aryl having 1 to 3 heteroatoms selected from the group consisting of N, O, and S as ring atoms, the remaining ring atoms being C. Said ring is a 5-membered ring, a 6-membered ring or a 6-membered/6-membered fused bicyclic ring. The examples of heteroaryl groups include furyl, thienyl, pyridyl, pyrrolyl, N-alkyl pyrrolyl, pyrimidinyl, pyrazinyl, imidazolyl, phthalazin-1-(2H)-one-yl-4, pyrido[3,2-d]pyridazin-5(6H)-one-yl-8, and the like. Said heteroaryl group may be optionally substituted with one or more groups which are each independently selected from the group consisting of halo, trihalomethyl, hydroxy, mercapto, alkylthio, amino, lower alkylamino, sulfonamide, cyano, alkoxyl, and alkyl.

The term "heterocyclic alkyl" refers to a monocyclic or fused ring group of 4 to 9 ring atoms, wherein one or two ring heteroatoms are selected from the group consisting of N, O, and S(O), (n is an integer ranging from 0 to 2), and the remaining ring atoms are C. In addition, the ring may also have one or more double bonds, but not have a completely conjugated pi-electron system. The unsubstituted heterocyclic alkyl includes, but is not limited to pyrrolidyl, piperidyl, piperazinyl, morpholinyl, thiomorpholinyl, homopiperazinyl, and the like. The heterocyclic alkyl may be substituted or unsubstituted. When substituted, the substituent group is preferably one or more, more preferably one, two, or three groups, even more preferably one or two groups, which are each independently selected from the group consisting of lower alkyl, $C_3$-$C_6$ cycloalkyl, trihaloalkyl, halo, hydroxy, lower alkoxy, cyano, and acyl. Preferably, the heterocyclic alkyl is optionally substituted with one or two groups independently selected from the group consisting of halo, lower alkyl, $C_3$-$C_6$ cycloalkyl, trihaloalkyl, hydroxy, mercapto, cyano, N-amido, and carboxy.

The term "heterocyclic ring" represented by Q refers to a heterocyclic group containing at least two nitrogen atoms as a member of the atoms forming the ring wherein the at least two nitrogen atoms independently bind to —CO-A-B group and —CO—CO—R group at the carbon atom of carbonyl, respectively. The heterocyclic ring may be mono-heterocyclic group, bridged-heterocyclic group, bi-heterocyclic group, or spiro-heterocyclic group.

The examples of mono-heterocyclic ring include but not limited to

The example of bridged-heterocyclic ring includes but not limited to

The examples of bi-heterocyclic ring include but not limited to

The examples of spiro-heterocyclic ring include but not limited to

The above mono-heterocyclic group, bridged-heterocyclic, bi-heterocyclic group or spiro-heterocyclic group may be substituted by one to four groups selected from the group consisting of halo, lower alkyl, $C_3$-$C_6$ cycloalkyl, trihaloalkyl, hydroxy, mercapto, cyano, amino, and carboxy.

The term "hydroxy" refers to an —OH group.

The term "alkoxyl" refers to both an —O-(alkyl) and an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

The term "haloalkoxy" refers to an —O-(haloalkyl). Representative examples include, but are not limited to, trifluoromethoxy, tribromomethoxy, and the like.

The term "aryloxyl" refers to both an —O-aryl and an —O-heteroaryl group, wherein the aryl and heteroaryl group are as defined above. Representative examples include, but are not limited to, phenoxy, pyridinyloxy, furanyloxy, thienyloxy, pyrimidinyloxy, pyrazinyloxy, and the like, and derivatives thereof.

The term "mercapto" refers to a —SH group.

The term "alkylthio" refers to a —S-(alkyl) and a —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "arylthio" refers to a —S-aryl and a —S-heteroaryl group, wherein the aryl and heteroaryl group are as defined above. Representative examples include, but are not limited to, e.g., phenylthio, pyridinylthio, furanylthio, thienylthio, pyrimidinylthio, and the like, and derivatives thereof.

The term "acyl" refers to a —C(O)—$R_3$ group, wherein $R_3$ is selected from the group consisting of hydrogen, lower alkyl, trihalomethyl, unsubstituted cycloalkyl, aryl (optionally substituted with one or more, preferably one, two, or three substituents selected from the group consisting of lower alkyl, trihalomethyl, lower alkoxy, and halo groups), heteroaryl (bonded through a ring carbon, and optionally substituted with one or more than one substituent, preferably one, two, or three substituents selected from the group consisting of lower alkyl, trihaloalkyl, lower alkoxy, and halo groups), and heteroalicyclic (bonded through a ring carbon, and optionally substituted with one or more than one substituent, preferably one, two, or three substituents selected from the group consisting of lower alkyl, trihaloalkyl, lower alkoxy, and halo groups). Representative acyl groups include, but are not limited to, acetyl, trifluoroacetyl, benzoyl, and the like.

The term "thioacyl" refers to a —C(S)—$R_3$ group, wherein $R_3$ is as defined above.

The term "acetyl" refers to a —C(O)$CH_3$ group.

The term "halo" refers to fluoro, chloro, bromo, or iodo, preferably fluoro or chloro.

The term "trifluoromethyl" refers to a —$CF_3$ group.

The term "cyano" refers to a —C≡N group.

The term "amino" refers to a —$NH_2$ group.

The term "carboxylic acid" refers to a —COOH group.

The term "carboxylic ester" refers to a —$COOR_3$ group, wherein $R_3$ is alkyl or cycloalkyl.

The term "hydroxyl alkyl" refers to a —$(CH_2)_r$OH group, wherein r is an integer ranging from 1 to 4.

The term "optional" or "optionally" means that the subsequently described event or circumstance may or may not occur, and that the description includes instances wherein the event or circumstance may or may not occur. For example, "aryl group optionally substituted with an alkyl group" means that the alkyl may or may not be present, that is, the description includes situations wherein the aryl group is substituted with an alkyl group and situations wherein the aryl group is not substituted with an alkyl group.

The term "pharmaceutical composition" refers to a mixture of one or more of the compounds of formula (I) as described in present invention herein, or hydrates, or solvates, or isomers, or physiologically/pharmaceutically acceptable salts or prodrugs thereof, with other chemical components, such as physiologically/pharmaceutically acceptable carriers and recipients. The purpose of a pharmaceutical composition is to facilitate administration of a compound to warm blood animals and human.

Synthesis of the Compounds of the Present Invention

The compounds of the present invention are prepared by procedures illustrated in the accompanying schemes.

Scheme-1

Compounds of formula (IB) may be synthesized by reacting a compound of formula (II) in which $R_1$ and $R_2$ are as previously defined, with a compound of formula (III) in which R is as previously defined, in the presence of a reagent such as HATU or HOBT/EDCI and a base such as DIPEA in a solvent such as DMF at a temperature in the range of 0 to the boiling point of the solvent used.

(IB)

(VI)

(IV)

Compounds of formula (II) may be synthesized by reacting a compound of formula (IV) in which $R_1$ and $R_2$ are as previously defined, with a compound of formula (V) in the presence of a reagents such as HATU or HOBT/EDCI in the presence of a base such as DIPEA in a solvent such as DMF at a temperature in the range of 0 to the boiling point of the solvent used, and then the protecting group of resulting product was deprotected by TFA in a solvent such as DCM at a temperature in the range of 0 to the boiling point of the solvent used.

Compounds of formula (VI) may be synthesized by coupling a compound of formula (VII) in which $R_2$ is as previously defined, with dimethyl hydrogen phosphite, and then reacting the resulting product with a compound of formula (VIII) in which $R_1$ is as previously defined via typical Wittig reaction.

(IV)

(VII)        (VIII)

(II)

(VI)

Compounds of formula (IV) may be synthesized by reacting a compound of formula (VI) in which $R_1$ and $R_2$ are as previously defined, with hydrazine in the presence of a base such as sodium hydroxide and a solvent such as water at a temperature in the range of 0 to the boiling point of the solvent used, then acidifying the resulting product by diluted HCl.

Compounds of formula (III), (V), and (VIII) are commercially available or may be synthesized by methods reported in the literature or textbook.

The present invention also relates to the compounds of formula (I), (IA), (IB), (IC), (ID), (IE), or isomers, or hydrates, or solvates, pharmaceutical composition containing them or pharmaceutically acceptable salts thereof, wherein the compounds of formula (I) may be present in free form or in the form of acid addition salts which are pharmaceutically acceptable and non-toxic. The pharmaceutically acceptable salts include hydrochloride, p-toluenesulfonate, tartarate, maleate, lactate, methanesulfonate, sulfate, phosphate, citrate, acetate, and trifluoroacetate, preferably p-toluenesulfonate, hydrochloride, tartarate, and trifluoroacetate.

Furthermore, the present invention relates to a pharmaceutical composition comprising the compounds of formula (I), (IA), (IB), (IC) (ID), (IE), or isomers, or hydrates, or salts thereof in a therapeutically effective dose, and a pharmaceutically acceptable carrier, adjuvant, or vehicle; And use of the compounds of the present disclosure or pharmaceutical acceptable salts thereof in the preparation of a medicament as a PARP inhibitor. In other words, this disclosure also provides a pharmaceutical composition comprising the above mentioned compounds in a therapeutically effective dose, as well as their use in the preparation of a medicament as a PARP inhibitor.

The compounds of formula (I) according to the present invention may be in crystalline or non-crystalline form. If the compound according to the present invention is in crystalline form, it may exist in a number of different polymorphic forms, and may optionally be hydrated or solvated. This invention includes within its scope stoichiometric hydrates as well as compounds containing variable amount of water. In general, the solvated forms, with pharmaceutically acceptable solvents such as water and ethanol among others are equivalent to the unsolvated forms for the purposes of this invention.

The compounds of formula (I) according to the present invention are useful in various pharmaceutically acceptable salt forms. The term "pharmaceutically acceptable sail" refers to those salt forms which would be apparent to the pharmaceutical chemist, i.e., those which are substantially non-toxic and provide the desired pharmacokinetic properties, palatability, absorption, distribution, metabolism or excretion. Other factors, more practical in nature, which are also important in the selection, are cost of the raw materials, and ease of crystallization, yield, stability, hygroscopicity and flowability of the resulting bulk drug. Conveniently, pharmaceutical compositions may be prepared from the active ingredients in combination with pharmaceutically acceptable carriers, adjuvants, or vehicles.

The pharmaceutically acceptable salts of the compounds of formula (I) include conventional non-toxic salts or quaternary ammonium salts of the compounds of formula (I) formed e.g. from non-toxic inorganic or organic acids. For example, non-toxic salts include those derived from inorganic acids such as hydrochloric, hydrobromic, sulfuric, sulfamic, phosphoric, nitric and the like; and the salts prepared from organic acids such as acetic, propionic, succinic, glyeolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like. The pharmaceutically acceptable salts of the present invention can be synthesized by conventional chemical methods.

Generally, the salts are prepared by reacting the free base or acid with a stoichiometric amount or an excess amount of the desired salt-forming inorganic or organic acid or base, in a suitable solvent or solvent combination. The compounds of formula (I) according to the present invention may have asymmetric centers and the present invention extents to all isometric forms including stereoisomer and geometric isomers of the compounds of formula (I), as well as enantiomers and mixtures thereof e.g. racemates. The different isomeric forms may be separated or resolved with each other by conventional methods, or any given isomer may be obtained by conventional synthetic methods or by stereospecific or asymmetric synthesis.

The invention described herein also includes a pharmaceutical composition which comprises a compound as described herein in combination with a pharmaceutically acceptable carrier, adjuvant, or vehicle.

The invention described herein also includes a method of treating a PARP mediated disease selected from cancer, vascular disease, inflammatory diseases, septic shock, ischaemic injury, diabetes, neurotoxicity, haemorraghic shock, and viral infection in a mammal, comprising administering to a mammalian patient in need of such treatment a compound as described herein in an amount which is effective to treat said PARP mediated disease.

The invention described herein also includes a method of treating cancer, which comprises administering to a mammalian patient in need of such treatment a compound as described herein in an amount which is effective to treat cancer.

This invention also relates to a method of inhibiting cancer in a mammal in need such treatment, which comprises administering to said mammal a compound of formula (I) in an amount which is effective for treating a range of cancers. Such method includes the treatment of the cancer of brain, genitourinary tract, lymphatic system, stomach, larynx, and lung. Additionally, such method includes the treatment of histiocytic lymphoma, breast cancer, ovary cancer, pancreatic cancer, liver cancer, prostate cancer, lung adenocarcinoma, and small cell lung cancers.

When administered to a patient for the purpose of the treatment of cancer, the dosage used can be varied depending upon the type of cancer, the age and general condition of the patient, the particular compound administered, the presence or level of toxicity or adverse effects experienced with the drug, and other factors. A representative example of a suitable dosage range is from as low as about 0.01 mg per kilogram body weight of the subject per day to as high as about 200 mg per kilogram body weight of the subject per day. However, the dosage administered is generally left to the discretion of the physician.

This invention also relates to a method of inhibiting a PARP in a mammal in need thereof, which comprises administering to said mammal an effective amount of a compound of formula (I) to inhibit said PARP down to normal levels, or in some cases to subnormal levels, so as to ameliorate, prevent or treat the disease state selected from cancer, vascular disease, diabetes, inflammatory diseases, septic shock, ischaemic injury, neurotoxicity, haemorraghic shock, and viral infection.

A compound of formula (I) according to the present invention can be administered alone or in combination with one or more other therapeutic agents, especially cytoxic agents and radiotherapy. Possible combination therapy may be administered by adopting the form of fixed combinations or by adopting administration of a compound of the invention and one or more other therapeutic agents being used or given independently of one another, or the combined administration of fixed combinations and one or more other therapeutic agents. A compound of formula (I) can besides or in addition be administered especially for tumor therapy in combination with chemotherapy, radiotherapy, surgical intervention, or a combination of these. Long term therapy is equally possible as an adjuvant therapy in the context of other treatment strategies, as described above. Other possible treatments are therapies maintaining the patient's status after tumor regression, or even chemopreventive therapies, for example in patients at risk.

When administered to a patient for the purpose of the treatment of a disease in which a PARP are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg per kilogram body weight of the subject per day to as high as about 200 mg per kilogram body weight of the subject per day. However, the dosage administered is generally left to the discretion of the physician.

The treatment methods are preferably carried out by delivering the compound of formula (I) parenterally. The term 'parenteral' as used herein includes oral dosing, intravenous, intramuscular, or intraperitoneal administration. The subcutaneous and intramuscular forms of parenteral administration are generally preferred. The present invention can also be carried out by delivering the compound of formula (I) subcutaneously, intranasally, intrarectally, transdermally or intravaginally.

The compounds of formula (I) may also be administered by inhalation. By 'inhalation' is meant intranasal and oral inhalation administration. Appropriate dosage forms for such administration, such as an aerosol formulation or a metered dose inhaler, may be prepared by conventional techniques.

The invention also relates to a pharmaceutical composition comprising a compound of formula (I) and a pharmaceutically acceptable carrier, adjuvant, or vehicle. The compounds of formula (I) may also be included in pharmaceutical compositions in combination with a second therapeutically active compound. The pharmaceutical carrier employed may be in the form of, for example, solid, liquid or gas. Examples of solid carriers include lactose, terra alba, sucrose, talc, gelatin, agar, pectin, acacia, magnesium stearate, stearic acid, and the like. Examples of liquid carriers are syrup, peanut oil, olive oil, water, and the like. Examples of gaseous carriers include, but not limited to, carbon dioxide and nitrogen. Similarly, the carrier or diluents may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carriers will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution. Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels, and the like. The amount of a compound of formula I used topically will, of course, vary with the compound chosen and the nature and severity of the condition, while can be varied in accordance with the discretion of the physician. A representative, topical, dose of a compound of formula (I) is from as low as about 0.01 mg to as high as about 2.0 g, administered one to four, preferably one to two times daily.

The active ingredient may comprise, for topical administration, from about 0.001% to about 10% w/w of the pharmaceutical composition according to the present invention.

Drops according to the present invention may comprise sterile or non-sterile aqueous or oily solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide, and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form with a greasy or non-greasy base, alone or in solution or suspension in an aqueous or non-aqueous liquid. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents, such as natural gums, cellulose derivatives or inorganic materials such as silicas, and other ingredients such as lanolin, may also be included.

Specific Implementation Methods

The following examples serve to illustrate the disclosure, but the examples should not be considered as limiting the scope of the disclosure.

EXAMPLES

The structures of all compounds were identified by nuclear magnetic resonance ($^1$HNMR) and mass spectrometry (MS). $^1$H NMR chemical shifts (δ) were recorded in ppm ($10^{-6}$). NMR was performed on a Varian Mercury-Plus-400 MHz spectrometer. The suitable solvents were deuterated-chloroform ($CDCl_3$), deuterated-dimethyl sulfoxide (DMSO-$d_6$) and deuterated-methanol ($CD_3OD$), with tetramethylsilane (TMS) as an internal standard, and chemical shifts were recorded in ppm ($10^{-6}$).

A low resolution MS was determined by a Themo Finnigan LCQ-Advantage mass spectrometer.

The average inhibiting activity of PARP enzyme $IC_{50}$ was determined by Thermo Electron Co., Vantaa, Finland.

Thin-layer silica gel was Yantai Huanghai HSGF254 or Qingdao GF254 silica gel plate.

Column chromatography generally used Yantai Huanghai 200-300 mesh silica gel as carrier.
DMSO-D$_6$: deuterated-dimethyl sulfoxide.
CDCl$_3$: deuterated-chloroform.
CD$_3$OD: deuterated-methanol Preparation of the Key Intermediates Preparation of 3,3,3-trifluoro-2-oxopropanoic acid To a solution of ethyl 3,3,3-trifluoro-2-oxopropanoate (5 g, 29.36 mmol) in ethanol (30 ml) was slowly added aqueous sodium hydroxide ((2.35 g, 58.72 mmol, dissolved in water (30 ml)), and stirred for 20 h at room temperature until the starting material was consumed. The reaction mixture was concentrated and the resulting white solid was dissolved in water (100 ml). The aqueous layer was extracted by ethyl acetate (50 ml×2), and then the aqueous layer was adjusted PH to 1~2 with concentrated HCl, and concentrated to give a white solid. The solid was added to methanol (200 ml) and stirred for overnight, filtered, and the filtrate was concentrated and dried to give the crude product (4.13 g, 99%) as a white solid, used in next step without further purification.

m/z [M−1]$^-$ 141.0

Preparation of 2-cyclopropyl-2-oxoacetic acid

The mixture of 1-cyclopropylethanone (10 g, 118.9 mmol), and sodium carbonate (145 mg, 1.36 mmol) in water (66 ml) was heated at 50, then the solution of KMnO$_4$ (19.8 g, 125.2 mmol) in water (594 ml) was slowly added over 10 h at this temperature, followed by adding methanol (90 ml). The mixture was filtered and the filtrate was concentrated to yield a white solid. The solid was added to acetone (80 ml) and heated for 30 min at 65, then cooled to room temperature, the white solid was precipitated and collected by filtration, dried to give the desired product (10 g, 74%) as a white solid.

m/z [M−1]$^-$ 113.0
$^1$HNMR (CD$_3$OD): δ 2.49-2.43 (1H, m), 1.06-0.98 (4H, m)

Preparation of 2-(furan-2-yl)-2-oxoacetic acid

To a suspension of 1-(furan-2-yl)ethanone (5 g, 45.5 mmol) in water (68 ml) was added concentrated HCl (22.3 ml) and heated at 65, then the aqueous sodium nitrite (22 g, 318.5 mmol, dissolved in water 107 ml) was added dropwisely over 2 h with the resulted PH at 3.0-3.5. After the mixture was heated at 65 for 1 h, another batch of aqueous sodium nitrite (1.4 g, 20 mmol, dissolved in water 7 ml) was added dropwisely and heated at 65 for another 40 min; the reaction was stopped and cooled to room temperature. 300 ml of DCM was added, and the aqueous phase was extracted with DCM (100 ml×3), the aqueous phase was adjusted PH to 0.5 by cond. HCl, and extracted by ethyl acetate (100 ml×3), the combined organic phase was washed by brine, dried over sodium sulphate, and concentrated to dryness, the residue was dissolved by small amount of ethyl acetate and petroleum ether, and kept at room temperature, the solid was precipitated out, washed by petroleum ether and dried to give the desired product (1.03 g, 16.2%) as brown solid.

m/z [M−1]$^-$ 139.0

Example 1

1-cyclopropyl-2-(4-(2-fluoro-5-((4-oxo-3,4-dihydrophthalazin-1-yl)methyl)benzoyl)piperazin-1-yl) ethane-1,2-dione Preparation of 2-fluoro-5-formylbenzonitrile To NMP (40 ml) were added 3-bromo-4-fluorobenzaldehyde (10 g, 0.05 mol) and CuCN (5 g, 0.055 mol). The resulting mixture was heated at 170 for 24 h until the reaction finished (monitored by TLC), and cooled to 80, 10 g of celite was added and stirred for 1 h at this temperature. The reaction mixture then was cooled to room temperature, and partitioned between ethyl acetate (250 ml) and water (125 ml), the organic phase was washed with water and brine, dried, filtered, and concentrated to give the crude. Then the crude was purified by column chromatography on silica gel (Petroleum ether:Ethyl Acetate=4:1) to afford target compound (8 g, 100%) as a light yellow solid.

$^1$HNMR (CDCl$_3$): δ 9.99 (1H, S), 8.18 (2H, m), 7.43 (1H, m).

Preparation of dimethyl (3-oxo-1,3-dihydroisobenzofuran-1-yl)phosphonate

To dry methanol (40 ml) was slowly added sodium (1.15 g, 50 mmol) at 0 under N$_2$ atmosphere while stirring, then added dimethyl hydrogen phosphite (5.5 g, 50 mmol), and 2-formylbenzoic acid (5.25 g, 35 mmol). The ice bath was removed and the reaction mixture was stirred for 30 min at room temperature, and then the reaction mixture was slowly added methanesulfonic acid (5.5 g, 55 mmol) and concentrated at reduced pressure to give the crude residue. The crude residue was partitioned between DCM and cold water (100 ml each), and the organic phase was washed with water and brine, dried over sodium sulphate, filtered, and concentrated to give the crude product (5.7 g, 67%) as an off white solid, used in next step without further purification.

$^1$HNMR (CDCl$_3$): δ 7.96 (1H, d), 7.75 (2H, m), 7.61 (1H, m), 5.73 (1H, d), 3.93 (3H, d), 3.60 (3H, d).

Preparation of 2-fluoro-5-((3-oxoisobenzofuran-1 (3H)-ylidene)methyl)benzonitrile To the solution of 2-fluoro-5-formylbenzonitrile (0.74 g, 5 mmol) and dimethyl 3-oxo-1,3-dihydroisobenzofuran-1-ylphosphonate (1.2 g, 5 mmol) in THF (30 ml) was added triethylamine (0.7 ml, 5 mmol) dropwise at a temperature of below 15° C., which was then slowly rose to ambient temperature and stirred for overnight. The reaction mixture was concentrated and the residue was added water and stirred for 30 min. The precipitated solid was collected by filtration, washed with water, hexane, and ether, and dried in vacuo to afford the target compound (1.2 g, 92.3%) as a light yellow solid (a 50:50 mixture of E and Z isomers), used in next step without further purification.

$^1$HNMR (CDCl$_3$): δ 8.13 (1H, m), 8.05 (1H, m), 7.98 (1H, m), 7.79 (2H, m), 7.61 (1H, m), 7.30 (1H, m), 6.35 (1H, s).

Preparation of 2-fluoro-5-((4-oxo-3,4-dihydrophthalazin-1-yl)methyl)benzoic acid To the mixture of 2-fluoro-5-((3-oxoisobenzofuran-1(3H)-ylidene)methyl)benzonitrile (1.2 g, 4.5 mmol) in water (6.5 ml) was added aqueous sodium hydroxide (0.84 g in 1.6 ml of water) drop-wise, then heated at 90 for 1 h. After cooled to 70, hydrazine hydrate (6.4 ml) was added and the reaction mixture was heated at 70 for overnight. Then the reaction mixture was cooled to room temperature, and adjusted to PH 3-4 by adding aqueous HCl (2N). The precipitated solid was collected by filtration, washed with water, and dried in vacuo to afford the target compound (0.9 g, 70%) as a pink solid, used in next step without further purification.

m/z [M−1]⁻ 296.90

¹HNMR (DMSO-d6): δ 13.22 (1H, brs), 12.61 (1H, s), 8.27 (1H, m), 7.99-7.81 (4H, m), 7.59 (1H, m), 7.25 (1H, m), 4.36 (2H, s)

Preparation of tert-butyl-4-(2-fluoro-5-((4-oxo-3,4-dihydrophthalazin-1-yl)methyl)benzoyl)piperazin-1-carboxylate 2-fluoro-5-((4-oxo-3,4-dihydrophthalazin-1-yl)methyl) benzoic acid (100 mg, 0.33 mmol), tert-butyl piperazine-1-carboxylate (187.3 mg, 1.0 mmol), HATU (255 mg, 0.67 mmol), and DIPEA (0.5 ml, 3.0 mmol) were dissolved in DMF (25 ml) and stirred at room temperature for 24 h. The reaction mixture was partitioned between DCM and water (50 ml each), and the organic phase was washed with aqueous sodium bicarbonate and brine, dried over sodium sulphate, filtered, and concentrated to get the crude product. Then the crude product was purified by column chromatography on silica gel (Petroleum ether:Ethyl Acetate=1:3) to afford target compound (100 mg, 64%) as a white solid.

¹HNMR (CDCl₃): δ 10.39 (1H, s), 8.47 (1H, m), 7.79-7.70 (3H, m), 7.34-7.26 (2H, m), 7.04 (1H, m), 4.28 (2H, s), 3.75-3.27 (8H, m), 1.47 (9H, s)

Preparation of 4-(4-fluoro-3-(piperazine-1-carbonyl) benzyl)phthalazin-1(2H)-one TFA salt To a solution of tert-butyl 4-(2-fluoro-5-((4-oxo-3,4-dihydrophthalazin-1-yl)methyl)benzoyl)piperazin-1-carboxylate (100 mg, 0.21 mmol) in DCM (20 ml) was added TFA (0.5 ml) and stirred for 6 h at room temperature. The reaction mixture was concentrated under vacuo to yield the crude product as a yellow solid, used in next step without further purification.

m/z [M+1]⁺ 367.3

Preparation of 1-cyclopropyl-2-(4-(2-fluoro-5-((4-oxo-3,4-dihydrophthalazin-1-yl)methyl)benzoyl) piperazin-1-yl)ethane-1,2-dione 4-(4-fluoro-3-(piperazine-1-carbonyl)benzyl)phthalazin-1(2H)-one TFA salt (1.24 g, 2.68 mmol), 2-cyclopropyl-2-oxoacetic acid (2.84 g, 24.84 mmol), DIPEA (6.9 ml, 41.4 mmol), and HATU (4.08 g, 10.8 mmol) were mixed in DMF (100 ml), the resulting reaction mixture was stirred at room temperature for overnight until the reaction finished (monitored by TLC). The reaction mixture was then partitioned between DCM and water (100 ml each, the water phase was extracted with DCM (100 ml). The combined organic phase was washed with water, sat. aqueous sodium bicarbonate, and brine, dried over sodium sulphate, filtered, and concentrated to yield the crude product. Then the crude product was purified by column chromatography on silica gel (DCM: MeOH=100:1) and re-crystallized from methanol to afford the desired product (610 mg, 49.3%) as a white solid.

m/z [M+1]⁺ 463.3

¹HNMR (CDCl₃): δ 10.46 (1H, brs), 8.48–8.46 (1H, m), 7.81–7.71 (3H, m), 7.36–7.30 (2H, m), 7.09–7.02 (1H, m), 4.29–4.27 (2H, d), 3.89–3.32 (8H, m), 2.44–2.31 (1H, m), 1.27–1.12 (4H, m).

Example 2

1-cyclopropyl-2-((1S,4S)-5-(2-fluoro-5-((4-oxo-3,4-dihydrophthalazin-1-yl)methyl)benzoyl)-2,5-diazabicyclo[2,2,1]heptan-2-yl)ethane-1,2-dione Preparation of (1S,4S)-tert-butyl 5-(2-fluoro-5-((4-oxo-3,4-dihydrophthalazin-1-yl)methyl)benzoyl)-2,5-diazabicyclo[2,2,1]heptane-2-carboxylate 2-fluoro-5-((4-oxo-3,4-dihydrophthalazin-1-yl)methyl) benzoic acid (400 mg, 1.32 mmol), (1S,4S)-tert-butyl 2,5-diazabicyclo[2,2,1]heptane-2-carboxylate (665 mg, 3.35 mmol), HATU (1.02 g, 2.68 mmol), and DI PEA (1.2 ml, 6.7 mmol) were dissolved in DMF (25 ml) and stirred at room temperature for 72 h. The reaction mixture was partitioned between DCM and water (50 ml each), and the organic phase was washed with aqueous sodium bicarbonate and brine, dried over sodium sulphate, filtered, and concentrated to get the crude product (1.23 g) as brown oil, used in next step without further purification.

m/z [M−1]⁻ 477.2

Preparation of 4-(3-((1S,4S)-2,5-diazabicyclo[2,2,1] heptane-2-carbonyl)-4-fluorobenzyl)phthalazin-1 (2H)-one TFA salt To the solution of (1S,4S)-tert-butyl 5-(2-fluoro-5-((4-oxo-3,4-dihydrophthalazin-1-yl)methyl)benzoyl)-2,5-diazabicyclo[2,2,1]heptane-2-carboxylate (1.23 g crude obtained from previous step) in DCM (50 ml) was added TFA (4 ml), and stirred for 16 h at room temperature. The reaction mixture was concentrated under vacuo to yield the crude product as yellow oil (2.64 g), used in next step without further purification.

m/z [M+1]⁺ 379.4

Preparation of 1-cyclopropyl-2-((1S,4S)-5-(2-fluoro-5-((4-oxo-3,4-dihydrophthalazin-1-yl)methyl)benzoyl)-2,5-diazabicyclo[2,2,1]heptan-2-yl)ethane-1,2-dione 4-(3-((1S,4S)-2,5-diazabicyclo[2,2,1]heptane-2-carbonyl)-4-fluorobenzyl)phthalazin-1 (2H)-one TFA salt (the crude obtained from previous step), 2-cyclopropyl-2-oxoacetic acid (917 mg, 8.04 mmol), DIPEA (1.5 ml, 12.06 mmol), and HATU (1.02 g, 2.68 mmol) were mixed in DMF (30 ml). After the resulting reaction mixture was stirred at room temperature for 24 h, the reaction mixture was partition between DCM and water (100 ml each). The aqueous phase was extracted with DCM (100 ml), and the combined organic phase was washed with water, sat. aqueous sodium bicarbonate and brine, dried over sodium sulphate, filtered, and concentrated to yield the crude product. The crude product was purified by column chromatography on silica gel (DCM: MeOH=40:1) to afford the desired product [(350 mg, 55% yield, based on 2-fluoro-5-((4-oxo-3,4-dihydrophthalazin-1-yl)methyl)benzoic acid (400 mg)] as an off white solid.

m/z [M+1]⁺ 475.4

¹H NMR (CDCl₃): δ 10.57–10.30 (1H, brs), 8.44 (1H, m), 7.77–7.63 (3H, m), 7.50–7.23 (2H, m), 7.05–6.92 (1H, m), 5.25–4.85 (2H, m), 4.50–4.48 (2H, d), 3.91–3.30 (4H, m), 2.94–2.68 (1H, m), 1.97–1.85 (2H, m), 1.20–0.96 (4H, m).

Example 3

1-cyclopropyl-2-(4-(2-fluoro-5-((4-oxo-3,4-dihydro-phthalazin-1-yl)methyl)benzoyl)-1,4-diazepan-1-yl)ethane-1,2-dione Preparation of tert-butyl 4-(2-fluoro-5-((4-oxo-3,4-dihydrophthalazin-1-yl)methyl)benzoyl)-1,4-diazepane-1-carboxylate 2-fluoro-5-((4-oxo-3,4-dihydrophthalazin-1-yl)methyl)benzoic acid (100 mg, 0.335 mmol), tert-butyl 1,4-diazepane-1-carboxylate (201 mg, 1 mmol), HATU (255 mg, 0.67 mmol), and DIPEA (0.5 ml, 2.88 mmol) were dissolved in DMF (30 ml) and stirred at room temperature for 24 h. The reaction mixture was partitioned between DCM and water (50 ml each), and the organic phase was washed with aqueous sodium bicarbonate, and brine, dried over sodium sulphate, filtered, and concentrated to get the crude product (370 mg) as brown oil, used in next step without further purification.

m/z [M-Boc]$^-$ 379

$^1$HNMR (CDCl$_3$): δ 10.55–10.44 (1H, m), 8.43 (1H, m), 7.76 (3H, m), 7.27 (2H, m), 7.05–6.98 (1H, m), 4.26 (2H, s), 3.78–3.26 (8H, m), 2.10–1.55 (2H, m), 1.47 (9H, s).

Preparation of 4-(3-(1,4-diazepane-1-carbonyl)-4-fluorobenzyl)phthalazin-1(2H)-one TFA salt To the solution of the crude tert-butyl 4-(2-fluoro-5-((4-oxo-3,4-dihydrophthalazin-1-yl)methyl)benzoyl)-1,4-diazepane-1-carboxylate (370 mg crude obtained from previous step) in DCM (20 ml) was added TFA (1 ml) and stirred for 14 h at room temperature. The reaction mixture was concentrated under vacuo to yield the crude product as yellow oil (300 mg), used in next step without further purification.

m/z [M+1]$^+$ 381

$^1$HNMR (CD$_3$OD): δ 8.36–8.34 (1H, m), 7.94–7.79 (3H, m), 7.52–7.48 (1H, m), 7.42–7.37 (1H, m), 7.19–7.15 (1H, m), 4.38 (2H, s), 3.95–3.23 (8H, m), 2.18–1.99 (2H, m).

Preparation of 1-cyclopropyl-2-(4-(2-fluoro-5-((4-oxo-3,4-dihydrophthalazin-1-yl)methyl)benzoyl)-1,4-diazepan-1-yl)ethane-1,2-dione 4-(3-(1,4-diazepane-1-carbonyl)-4-fluorobenzyl)phthalazin-1(2H)-one TFA salt (the crude obtained from previous step), 2-cyclopropyl-2-oxoacetic acid (230 mg, 2.01 mmol), DIPEA (0.5 ml, 2.9 mmol), and HATU (255 mg, 0.67 mmol) were mixed in DMF (20 ml). After the resulting reaction mixture was stirred at room temperature for 20 h, the reaction mixture was partition between DCM and water (100 ml each). The aqueous phase was extracted with DCM (100 ml), and the combined organic phase was washed with water, sat. aqueous sodium bicarbonate, and brine, dried over sodium sulphate, filtered, and concentrated to yield the crude product. Then the crude product was purified by column chromatography on silica gel (DCM:MeOH=80:1) to afford the desired product [(38 mg, 24% yield, based on 2-fluoro-5-((4-oxo-3,4-dihydrophthalazin-1-yl)methyl)benzoic acid (100 mg)] as an off white solid.

m/z [M+1]$^+$ 477.1

$^1$HNMR (CDCl$_3$): δ 10.30 (1H, brs), 8.45–8.43 (1H, m), 7.80–7.69 (3H, m), 7.30–7.22 (2H, m), 7.07–6.99 (1H, m), 4.27–4.26 (2H, d), 3.86–3.31 (8H, m), 2.39–2.35 (1H, m), 1.71–1.88 (2H, m), 1.28–1.09 (4H, m).

Example 4

1-(4-(2-fluoro-5-((4-oxo-3,4-dihydrophthalazin-1-yl)methyl)benzoyl)piperazin-1-yl)-2-phenylethane-1,2-dione 4-(4-fluoro-3-(piperazine-1-carbonyl)benzyl)phthalazin-1(2H)-one TFA salt (311 mg, 0.65 mmol), 2-oxo-2-phenylacetic acid (900 mg, 6 mmol), DIPEA (2 ml, 11.6 mmol), and HATU (1010 mg, 2.65 mmol) were mixed in DMF (50 ml), the resulting reaction mixture was stirred at room temperature for 4 days until the reaction finished (monitored by TLC). The reaction mixture was then partitioned between DCM and water (100 ml each, the water phase was extracted with DCM (100 ml)). The combined organic phase was washed with water, sat. aqueous sodium bicarbonate, and brine, dried over sodium sulphate, filtered, and concentrated to yield the crude product. Then the crude product was firstly purified by column chromatography on silica gel (DCM:MeOH=100:1) and re-purified by preparative TLC (DCM:MeOH=40:1) to afford the desired product (110 mg, 32.9%) as an off white solid.

m/z [M+1]$^+$ 499.1

$^1$HNMR (CDCl$_3$): δ 10.15 (1H, brs), 8.49–8.42 (1H, m), 7.95–7.91 (2H, m), 7.77–7.66 (4H, m), 7.64–7.48 (2H, m), 7.33–7.25 (2H, m), 7.08–6.85 (1H, m), 4.28–4.24 (2H, d), 3.98–3.32 (8H, m).

Example 5

1-(4-(2-fluoro-5-((4-oxo-3,4-dihydrophthalazin-1-yl)methyl)benzoyl)piperazin-1-yl)-3,3-dimethylbutane-1,2-dione 4-(4-fluoro-3-(piperazine-1-carbonyl)benzyl)phthalazin-1(2H)-one TFA salt (310 mg, 0.65 mmol), 3,3-dimethyl-2-oxobutanoic acid [1.37 g (60%), 6.3 mmol], DIPEA (2 ml, 11.6 mmol), and HATU (1030 mg, 2.72 mmol) were mixed in DMF (50 ml), the resulting reaction mixture was stirred at room temperature for 44 h until the reaction finished (monitored by TLC). The reaction mixture was then partitioned between DCM and water (100 ml each, the water phase was extracted with DCM (100 ml). The combined organic phase was washed with water, sat. aqueous sodium bicarbonate, and brine, dried over sodium sulphate, filtered, and concentrated to yield the crude product. Then the crude product was firstly purified by column chromatography on silica gel (DCM:MeOH=100:1) and re-purified by preparative TLC (DCM:MeOH=40:1) to afford the desired product (150 mg, 46.9%) as a off white solid.

m/z [M+1]$^+$ 479.1

$^1$HNMR (CDCl$_3$): δ 10.06 (1H, brs), 8.45–8.43 (1H, m), 7.77–7.68 (3H, m), 7.32–7.28 (2H, m), 7.07–6.99 (1H, m), 4.27–4.26 (2H, d), 3.92–3.16 (8H, m), 1.28–1.24 (9H, d).

Example 6

1-(4-(2-fluoro-5-((4-oxo-3,4-dihydrophthalazin-1-yl)methyl)benzoyl)-1,4-diazepan-1-yl)-3,3-dimethylbutane-1,2-dione 4-(3-(1,4-diazepane-1-carbonyl)-4-fluorobenzyl)phthalazin-1(2H)-one TFA salt (320 mg, 0.65 mmol), 3,3-dimethyl-2-oxobutanoic acid [1.6 g (60%), 7.39 mmol], DIPEA (3 ml, 17.4 mmol), and HATU (1.5 g, 3.92 mmol) were mixed in DMF (50 ml). After the resulting reaction mixture was stirred at room temperature for 87 h, the reaction mixture was partition between DCM and water (100 ml each). The aqueous phase was extracted with DCM (100 ml), and the combined organic phase was washed with water, sat. aqueous sodium bicarbonate, and brine, dried over sodium sulphate, filtered, and concentrated to yield the crude product. Then the crude product was purified by preparative TLC (EA:PE=1:1) to afford the desired product (30 mg, 9.1%) as an off white solid.

m/z [M+1]$^+$ 493.4

$^1$HNMR (CDCl$_3$): δ 8.49 (1H, m), 7.76–7.70 (3H, m), 7.35–7.24 (2H, m), 7.04–7.02 (1H, m), 4.31–4.28 (2H, m), 3.91–3.20 (8H, m), 1.95–1.72 (2H, m), 1.27 (9H, m).

Example 7

1-(4-(2-fluoro-5-((4-oxo-3,4-dihydrophthalazin-1-yl) methyl)benzoyl)-1,4-diazepan-1-yl)-2-phenylethane-1,2-dione 4-(3-(1,4-diazepane-1-carbonyl)-4-fluorobenzyl)phthalazin-1(2H)-one TFA salt (320 mg, 0.65 mmol), 2-oxo-2-phenylacetic acid (1.4 g, 9.32 mmol), DIPEA (3 ml, 17.4 mmol), and HATU (1.8 g, 4.72 mmol) were mixed in DMF (50 ml). After the resulting reaction mixture was stirred at room temperature for 85 h, the reaction mixture was partition between DCM and water (100 ml each). The aqueous phase was extracted with DCM (100 ml), and the combined organic phase was washed with water, sat. aqueous sodium bicarbonate, and brine, dried over sodium sulphate, filtered, and concentrated to yield the crude product. Then the crude product was purified by preparative TLC (Petroleum ether:Ethyl Acetate=1:1 to 1:2) to afford the desired product (140 mg, 41%) as a light yellow solid.

m/z [M+1]$^+$ 513.4

$^1$HNMR (CDCl$_3$): δ 10.41 (1H, brs), 8.46–8.38 (2H, m), 7.95–7.87 (2H, m), 7.79–7.60 (4H, m), 7.53–7.45 (2H, m), 7.39–7.22 (2H, m), 7.08–6.95 (1H, m), 4.31–4.28 (2H, d), 3.93–3.30 (8H, m), 1.78–1.62 (2H, m).

Example 8

1-(4-(2-fluoro-5-((4-oxo-3,4-dihydrophthalazin-1-yl) methyl)benzoyl)-1,4-diazepan-1-yl)-2-(furan-2-yl) ethane-1,2-dione 4-(3-(1,4-diazepane-1-carbonyl)-4-fluorobenzyl)phthalazin-1(2H)-one TFA salt (320 mg, 0.65 mmol), 2-(furan-2-yl)-2-oxoacetic acid (563 mg, 4 mmol), DIPEA (1 ml, 6 mmol), and HATU (510 mg, 1.34 mmol) were mixed in DMF (30 ml). After the resulting reaction mixture was stirred at room temperature for 60 h, the reaction mixture was partition between DCM and water (100 ml each). The aqueous phase was extracted with DCM (100 ml), and the combined organic phase was washed with water, sat. aqueous sodium bicarbonate, and brine, dried over sodium sulphate, filtered, and concentrated to yield the crude product. Then the crude product was purified by column chromatography on silica gel (Petroleum ether:Ethyl Acetate=1:3) to afford the desired product (111 mg, 31%) as a light yellow solid.

m/z [M+1]$^+$ 503.3

1 HNMR (CDCl$_3$): δ 10.61 (1H, brs), 8.46–8.40 (1H, m), 7.78–7.67 (4H, m), 7.40–7.26 (3H, m), 7.08–6.96 (1H, m), 6.61–6.58 (1H, m), 4.27 (2H, s), 3.90–3.34 (8H, m), 2.17–1.99 (2H, m).

Example 9

1-(4-(2-fluoro-5-((4-oxo-3,4-dihydrophthalazin-1-yl) methyl)benzoyl)piperazin-1-yl)-2-(furan-2-yl) ethane-1,2-dione 4-(4-fluoro-3-(piperazine-1-carbonyl)benzyl)phthalazin-1(2H)-one TFA salt (155 mg, 0.32 mmol), 2-(furan-2-yl)-2-oxoacetic acid (278 mg, 1.98 mmol), DIPEA (0.5 ml, 3 mmol), and HATU (251 mg, 0.66 mmol) were mixed in DMF (30 ml), the resulting reaction mixture was stirred at room temperature for 45 h until the reaction finished (monitored by TLC). The reaction mixture was then partitioned between DCM and water (100 ml each, and the water phase was extracted with DCM (50 ml). The combined organic phase was washed with water, sat. aqueous sodium bicarbonate, and brine, dried over sodium sulphate, filtered, and concentrated to yield the crude product. Then the crude product was purified by column chromatography on silica gel (Petroleum ether:Ethyl Acetate=1:3) to afford the desired product (20 mg, 20.4%) as a light yellow solid.

m/z [M+1]$^+$ 489.2

1HNMR (CDCl$_3$): δ 10.56 (1H, brs), 8.45 (1H, s), 7.77-7.70 (4H, m), 7.50-7.32 (3H, m), 7.07-6.98 (1H, m), 6.61 (1H, s), 4.29 (2H, s), 3.82-3.36 (8H, m).

Example 10

1-((1S,4S)-5-(2-fluoro-5-((4-oxo-3,4-dihydrophthalazin-1-yl)methyl)benzoyl)-2,5-diazabicyclo [2.2.1]hepta n-2-yl)-2-(furan-2-yl)ethane-1,2-dione 4-(3-((1S,4S)-2,5-diazabicyclo[2,2,1]heptane-2-carbonyl)-4-fluorobenzyl)phthalazin-1 (2H)-one TFA salt (200 mg, 0.41 mmol), 2-(furan-2-yl)-2-oxoacetic acid (352 mg, 2.52 mmol), DIPEA (0.63 ml, 3.78 mmol), and HATU (320 mg, 0.84 mmol) were mixed in DMF (30 ml). After the resulting reaction mixture was stirred at room temperature for 60 h, the reaction mixture was partition between DCM and water (100 ml each). The aqueous phase was extracted with DCM (100 ml), and the combined organic phase was washed with water, sat. aqueous sodium bicarbonate, and brine, dried over sodium sulphate, filtered, and concentrated to yield the crude product. Then the crude product was purified by column chromatography on silica gel (Petroleum ether:Ethyl Acetate=1:3) to afford the desired product (106 mg, 50.5%) as a light yellow solid.

m/z [M+1]$^+$ 501.4

1HNMR (CDCl$_3$): δ 10.61 (1H, brs), 8.46 (1H, s), 7.81–7.62 (6H, m), 7.60–7.26 (1H, m), 7.25–6.98 (1H, m), 6.60 (1H, s), 4.30 (2H, s), 3.94–3.38 (6H, m), 2.04–1.89 (2H, m).

Example 11

1-(4-(2-fluoro-5-((4-oxo-3,4-dihydrophthalazin-1-yl) methyl)benzoyl)piperazin-1-yl)propane-1,2-dione 4-(4-fluoro-3-(piperazine-1-carbonyl)benzyl)phthalazin-1(2H)-one TFA salt (157.5 mg, 0.34 mmol), 2-oxopropanoic acid (0.15 ml (d=1.26), 2.15 mmol), DIPEA (0.5 ml, 3 mmol), and HATU (258.6 mg, 0.68 mmol) were mixed in DMF (20 ml), the resulting reaction mixture was stirred at room temperature for 60 h until the reaction finished (monitored by TLC). The reaction mixture was then partitioned between DCM and water (50 ml each, the water phase was extracted with DCM (50 ml). The combined organic phase was washed with water, sat. aqueous sodium bicarbonate, and brine, dried over sodium sulphate, filtered, and concentrated to yield the crude product. Then the crude product was purified by column chromatography on silica gel (Petroleum ether: Ethyl Acetate=1:2) to afford the desired product (20 mg, 13.5%) as a light yellow solid.

m/z [M+1]$^+$ 437.3

$^1$H NMR (CDCl$_3$): δ 11.10 (1H, brs), 8.47–8.45 (1H, d), 7.78–7.69 (3H, m), 7.35–7.25 (2H, m), 7.07–7.00 (1H, m), 4.29 (2H, s), 3.82–3.35 (8H, m), 2.46–2.43 (3H, d).

Example 12

1-(4-(2-fluoro-5-((4-oxo-3,4-dihydrophthalazin-1-yl)methyl)benzoyl)-1,4-diazepan-1-yl)propane-1,2-dione 4-(3-(1,4-diazepane-1-carbonyl)-4-fluorobenzyl)phthalazin-1(2H)-one TFA salt (320 mg, 0.65 mmol), 2-oxopropanoic acid [0.3 ml (d=1.26), 4.29 mmol], DIPEA (1 ml, 6 mmol), and HATU (510 mg, 1.34 mmol) were mixed in DMF (30 ml). After the resulting reaction mixture was stirred at room temperature for 60 h, the reaction mixture was partition between DCM and water (100 ml each). The aqueous phase was extracted with DCM (100 ml), and the combined organic phase was washed with water, sat. aqueous sodium bicarbonate, and brine, dried over sodium sulphate, filtered, and concentrated to yield the crude product. Then the crude product was purified by column chromatography on silica gel (Petroleum ether:Ethyl Acetate=1:2) to afford the desired product (136 mg, 45.1%) as an off white solid.

m/z [M+1]$^+$ 451.3

$^1$H NMR (CDCl$_3$): δ 10.99 (1H, brs), 8.46 (1H, m), 7.76 (3H, m), 7.25–7.01 (3H, m), 4.28 (2H, s), 3.85–3.33 (8H, m), 2.44 (3H, s).

Example 13

3,3,3-trifluoro-1-(4-(2-fluoro-5-((4-oxo-3,4-dihydro-phthalazin-1-yl)methyl)benzoyl)piperazin-1-yl)propane-1,2-dione The title compound was prepared according to the procedure of Example 1 as a light yellow solid.

m/z [M+1]$^+$ 491.2

Example 14

3,3,3-trifluoro-1-(4-(2-fluoro-5-((4-oxo-3,4-dihydro-phthalazin-1-yl)methyl)benzoyl)-1,4-diazepan-1-yl)propane-1,2-dione The title compound was prepared according to the procedure of Example 3 as a light yellow solid.

m/z [M+1]$^+$ 505.2

Example 15

1-((1S,4S)-5-(2-fluoro-5-((4-oxo-3,4-dihydro-phthalazin-1-yl)methyl)benzoyl)-2,5-diazabicyclo[2.2.1]hepta n-2-yl)-3,3-dimethylbutane-1,2-dione The title compound was prepared according to the procedure of Example 2 as a light yellow solid m/z [M+1]$^+$ 491.2

Example 16

1-((1S,4S)-5-(2-fluoro-5-((4-oxo-3,4-dihydro-phthalazin-1-yl)methyl)benzoyl)-2,5-diazabicyclo[2.2.1]hepta n-2-yl)-2-phenylethane-1,2-dione The title compound was prepared according to the procedure of Example 2 as a light yellow solid.

m/z [M+1]$^+$ 511.2

The invention compounds of formula (I), and hydrates, solvates, isomers, or the salts thereof having the efficacy of inhibiting PARP can be assessed by the following assays:

A: PARP Inhibition Assessment

Evaluate the inhibitory effect of tested compounds on PARP activity, and calculate the IC$_{50}$ values. 3-Aminobenzamide (TREVIGEN, MD, USA) was used as positive reference drug.

HT Universal Colorimetric PARP Assay Kit With Histones and Coating Buffer (TREVIGEN, Cat #4671-096-K) was employed to test the inhibitory activity possessed by the test compounds (from Shanghai De Novo Pharmatech Co Ltd. 上海迪诺医药科 技有限公司).

Protocol

Plate Coating

Adding 50 µl aliquot of diluted histones per well of the clear protein-binding plate, covering the plate with a lid, adhesive plate cover, or parafilm, and incubating it overnight at 4° C.

Plate Blocking

The plate is washed 4 times with 1×PBS (Sangon Biotech, Shanghai)+0.1% Triton X-100(Sangon Biotech, Shanghai) (200 µl/well), blocked by adding 100 µl of 1× Strep-Diluent to every well, and incubated at room temperature for 1 hour or overnight at 4° C., covered. Then the plate is washed 4 times with 1×PBS+0.1% Triton X-100 (200 µl/well) again.

Ribosylation Reaction

After removed the strip wells from the wrapper, the wells is added serial dilutions of inhibitor of interest. Then the wells containing inhibitor is added diluted PARP enzyme (1 Unit/well), and incubated for 10 minutes at room temperature. Each well is added 25 µl of 1×PARP Cocktail, and incubated at room temperature for 30-60 minutes.

The activity control is 1 Unit/well PARP-HSA without inhibitors. These wells provide the 100% activity reference point. The use of histone-coated wells should be included as positive controls if other test proteins are used.

The negative control is prepared without PARP, to determine background absorbance.

Distributing 25 µl of 1×PARP Cocktail into each well using a multichannel pipettor, and incubating the plate at room temperature for 30-60 minutes.

Detection

After washed 4 times with 1×PBS+0.1% Triton X-100 (200 µl/well), each well is added 50 µl diluted Strep-HRP, and incubated at room temperature for 20 minutes. Then the plate is washed 4 times with 1×PBS+0.1% Triton X-100 (200 µl/well), again. Each well is added 50 µl TACS-Sapphire™ colorimetric substrate, and incubated, in the dark, for 10-30 minutes. Color development should be monitored for observable blue color in the wells and the plate is read at 630 nm on a 96-well plate reader with 630 nm or 450 nm filters (Thermo Electron Co., Vantaa, Finland). The reaction can be stopped by adding 50 µl per well of 0.2 M HCl and the absorbance is read at 450 nm.

Result:

All the compounds exhibited PARP-inhibition activities in vitro, which were much more potent than that of 3-Aminobenzamide. The tested compounds have IC$_{50}$ ranged from 6.6 nM to 200 nM for the PARP inhibition, while 3-Aminobenzamide only has IC$_{50}$ is 51.0 μM.

B. V-C8 (BRCA2-Deficient) and V-C8#13-5 (BRCA2-Competent) Cells Proliferation Assays.

The following methods can be used to measure the activities of the compounds according to the present invention that inhibit the enzymatic activity of PARP.

V-C8 (BRCA2-deficient) and V-C8#13-5 (BRCA2-competent) cells were maintained in F10 medium supplemented with 10% FBS. Cells were plated in 96-well plates at 1×10$^4$ cells per ml and allowed to adhere to the plate overnight. Cells were incubated in the presence of the drug (including the compounds according to the present invention and the positive control drug) for 120 h and cell survival was determined by sulforhodamine B(SRB) assay (Skehan P, et al. J. Natl. Cancer Inst 1990; 82: 1107-1112). The optical density of each sample was read on a microplate reader at 510 nm.

The compounds of the present invention are tested for their ability to inhibit the enzyme activity of PARP. The inhibitory rate or the half inhibition concentration IC$_{50}$ (concentration of test compound at which 50% of the enzyme activity is inhibited) for each compound is determined by incubating fixed amounts of mixed enzyme substrate with several different concentrations of test compounds.

IC$_{50}$ of the PARP inhibition of the test compounds were ranged from 42 nM to 200 nM

CONCLUSION

The tested compounds have strong inhibitory activity of PARP.

C: Animal Model Assays

Figure 1:
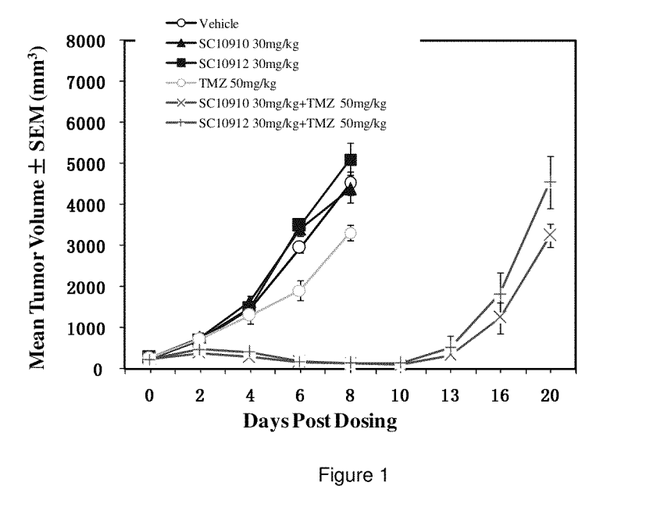
FIG. 1 shows the result of aminal model assays, wherein the mean tumor volume of the mice treated with either vehicle, compounds, temozolomide (TMZ) alone or in combination is measured and ploted versus the dosing days. It can be seen that the combination of TMZ and the compounds of the present invention has significantly synergic effect.
Figure 2:
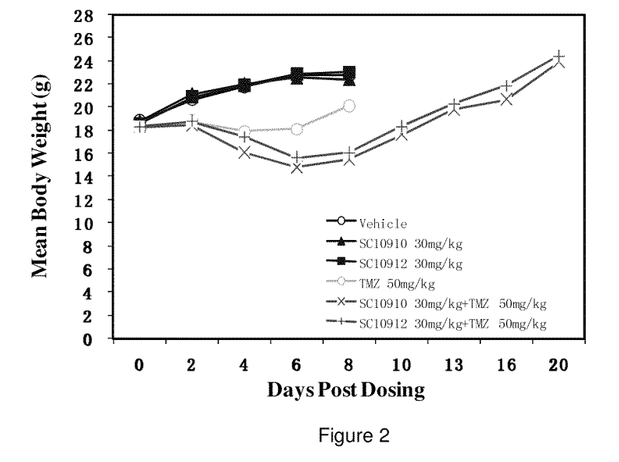
FIG. 2 shows the result of aminal model assays, wherein the mean body weight of the mice treated with either vehicle, compounds, temozolomide (TMZ) alone or in combination is measured and ploted versus the dosing days.

Experimental Procedure:

Female nude mice (Balb/cA-nude, 6-7 weeks old) were purchased from Shanghai Laboratory Animal Center, Chinese Academy of Sciences, Shanghai, China. Mice were housed under pathogen-free conditions with autoclaved rodent chow and water available ad libitum. Each mouse was inoculated s.c. with breast cancer MX-1 cells in 0.1 ml PBS over the left flank. When the tumor volume reached 200-350 mm$^3$, mice were randomized based on initial tumor volume measurements and treated with either vehicle, compounds, temozolomide (TMZ) alone or in combination. Tumor volumes were measured with electronic digital caliper and calculated using the formula length (mm)×width (mm)$^2$/2 and expressed in mm$^3$. Student's t-test was used to evaluate the statistical significance of observed differences.

Results are shown in FIGS. 1 and 2. FIG. 1 shows the result of aminal model assays, wherein the mean tumor volume of the mice treated with either vehicle, compounds, temozolomide (TMZ) alone or in combination is measured and ploted versus the dosing days. It can be seen that the combinational administration of TMZ and the compounds of the present invention has signicficantly synergic effect.

FIG. 2 shows the result of aminal model assays, wherein the mean body weight of the mice treated with either vehicle, compounds, temozolomide (TMZ) alone or in combination is measured and ploted versus the dosing days.

The invention claimed is:

1. A compound of formula (IA), or a stereoisomer or pharmaceutically acceptable salt thereof:

(IA)

wherein:
Z is C—R$_1$ or N;
Q is a heterocyclic ring which contains at least two nitrogen atoms as a member of the atoms forming the ring wherein the at least two nitrogen atoms independently bind to the —CO-substituted aryl group and the —CO—CO—R group at the carbon atom of the carbonyl, respectively; and Q is selected from the group consisting of monocyclic heterocyclyl, bridged-heterocyclyl, bicyclic heterocyclyl, and spirocyclic heterocyclyl;
R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl and heteroaryl or substituted heteroaryl, said substituents are selected from the group consisting of halo, lower alkyl, amino, lower alkylamino, lower alkyl alkoxy, haloalkoxy, hydroxy, amido, aminocarbonyl, sulfonamido, cyano, alkynyl, alkoxy, aryloxy, carboxy, and carboxylate;
R$_1$ is hydrogen, fluoro or chloro; and
R$_2$ is hydrogen.

2. The compound according to claim 1, in which the compound is a compound of formula (IB), or a stereoisomeror or pharmaceutically acceptable salt thereof:

(IB)

wherein:
R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl, and heteroaryl or substituted het- eroaryl, said substituents are selected from the group consisting of halo, lower alkyl, amino, lower alkylamino, lower alkyl alkoxy, haloalkoxy, hydroxy, amido, aminocarbonyl, sulfonamido, cyano, alkynyl, alkoxy, aryloxy, carboxy, and carboxylate;

R₁ is hydrogen, fluoro or chloro; and

R₂ is hydrogen;

represents a heterocyclic group selected from the group consisting of:

.

3. The compound according to claim 1, in which the compound is a compound of formula (IC), formula (ID), or formula (IE), or a stereoisomer or pharmaceutically acceptable salt thereof:

(IC)

(ID)

(IE)

wherein:

R is selected from the group consisting of alkyl or substituted alkyl, alkenyl or substituted alkenyl, alkynyl or substituted alkynyl, cycloalkyl or substituted cycloalkyl, heterocycloalkyl or substituted heterocycloalkyl, aryl or substituted aryl, and heteroaryl or substituted heteroaryl, said substituents are selected from the group consisting of halo, lower alkyl, amino, lower alkylamino, and lower alkyl alkoxy, haloalkoxy, hydroxy, amido, aminocarbonyl, sulfonamido, cyano, alkynyl, alkoxy, aryloxy, carboxy, and carboxylate; and

R₁ is hydrogen, fluoro or chloro; and

R₂ is hydrogen.

4. The compound according to claim 1, in which the compound is a compound of formula (IF), formula (IG), or formula (IH), or a stereoisomer or pharmaceutically acceptable salt thereof:

(IF)

(IH)

(IG)

wherein:
R is selected from the group consisting of methyl, trifluoromethyl, tert-butyl, cyclopropyl, furan-2-yl, or phenyl.

5. A pharmaceutical composition comprising a compound according to claim 1 and a pharmaceutically acceptable carrier, adjuvant, or vehicle.

6. A method for treating cancer in a subject, comprising administering to said subject a therapeutically effective amount of a compound of claim 1, wherein said cancer is deficient in a homologous recombination dependent deoxyribonucleic acid double strand break repair pathway and said method is performed by inhibiting poly(adenosine diphosphate-ribose) polymerase.

7. The method according to claim 6, wherein said cancer involves cells which are deficient in breast cancer gene 1 or breast cancer gene 2.

* * * * *